(12) United States Patent
Egan et al.

(10) Patent No.: US 9,833,192 B2
(45) Date of Patent: Dec. 5, 2017

(54) FINGER MOUNTED PHYSIOLOGY SENSOR

(71) Applicant: Thought Technology Ltd., Montreal West (CA)

(72) Inventors: Eamon Egan, Montreal (CA); Harold Myers, Montreal (CA); David Muir, Montreal (CA); Andre Arnold, Montreal (CA)

(73) Assignee: THOUGHT TECHNOLOGY LTD., Montréal (CA)

( * ) Notice: Subject to any disclaimer, the term of this patent is extended or adjusted under 35 U.S.C. 154(b) by 311 days.

(21) Appl. No.: 14/213,037

(22) Filed: Mar. 14, 2014

(65) Prior Publication Data

US 2014/0275845 A1 Sep. 18, 2014

Related U.S. Application Data

(60) Provisional application No. 61/792,326, filed on Mar. 15, 2013.

(51) Int. Cl.

| | |
|---|---|
| *A61B 5/0295* | (2006.01) |
| *A61B 5/00* | (2006.01) |
| *A61B 5/0205* | (2006.01) |
| *A61B 5/024* | (2006.01) |
| *A61B 5/053* | (2006.01) |

(52) U.S. Cl.
CPC ........ *A61B 5/6826* (2013.01); *A61B 5/02055* (2013.01); *A61B 5/02427* (2013.01); *A61B 5/0531* (2013.01)

(58) Field of Classification Search
CPC . A61B 5/6824–5/6826; A61B 5/02055; A61B 5/02427; A61B 5/0531; A61B 5/00; A61B 5/486; A61B 5/6801–5/6802; A61B 5/6806; A61B 5/6831; G06F 19/30; G06F 19/345
USPC .................................................. 600/300–301
See application file for complete search history.

(56) References Cited

U.S. PATENT DOCUMENTS

| | | | |
|---|---|---|---|
| 3,841,316 A | 10/1974 | Meyer | |
| 3,916,877 A | 11/1975 | Beckman | |
| 3,999,537 A | 12/1976 | Noiles | |
| 4,036,211 A | 7/1977 | Veth et al. | |
| 4,246,906 A | 1/1981 | Winberg et al. | |
| 4,450,843 A * | 5/1984 | Barney | A61B 5/02438 600/483 |
| 4,625,732 A | 12/1986 | Kasa et al. | |

(Continued)

*Primary Examiner* — Gary Jackson
*Assistant Examiner* — Dacheng Xie
(74) *Attorney, Agent, or Firm* — Norton Rose Fulbright Canada LLP

(57) ABSTRACT

The described physiology sensor is worn on a single finger to capture one or more different physiological signals and has a sensor body including first and second raised mounds, protruding from its surface and being longitudinally spaced-apart such as to define a transverse air gap therebetween. The mounds each retain electrodes which abut palmar surfaces of the single finger. The sensor also has one or more physiological sensing devices housed within the body, including a skin conductance sensing device. The sensor can also have at least one of a temperature sensing device, and a photoplethysmography sensing device. A processor is housed within the body and communicates with the electrodes and the sensing devices to apply an electrical excitation thereto, and to process the physiological measurements.

20 Claims, 5 Drawing Sheets

(56) References Cited

U.S. PATENT DOCUMENTS

| | | | |
|---|---|---|---|
| 5,109,849 A | 5/1992 | Goodman et al. | |
| 6,026,322 A | 2/2000 | Korenman et al. | |
| 6,288,707 B1* | 9/2001 | Philipp | G06F 3/0213 341/22 |
| 6,516,289 B2 | 2/2003 | David | |
| 6,526,315 B1 | 2/2003 | Inagawa et al. | |
| 6,553,245 B1 | 4/2003 | Grace et al. | |
| 7,894,888 B2 | 2/2011 | Chan et al. | |
| 2002/0099277 A1 | 7/2002 | Harry et al. | |
| 2002/0156381 A1 | 10/2002 | Kao et al. | |
| 2003/0023145 A1 | 1/2003 | Lee et al. | |
| 2004/0039418 A1* | 2/2004 | Elstrom | A61B 5/0048 607/3 |
| 2005/0038328 A1 | 2/2005 | Stoehrer et al. | |
| 2007/0060824 A1 | 3/2007 | Lam et al. | |
| 2007/0299322 A1 | 12/2007 | Miyajima et al. | |
| 2008/0081963 A1 | 4/2008 | Naghavi et al. | |
| 2008/0091089 A1 | 4/2008 | Guillory et al. | |
| 2008/0091090 A1 | 4/2008 | Guillory et al. | |
| 2008/0171918 A1 | 7/2008 | Teller et al. | |
| 2008/0177158 A1 | 7/2008 | Teller et al. | |
| 2008/0183052 A1 | 7/2008 | Teller et al. | |
| 2008/0208016 A1* | 8/2008 | Hughes | A61B 5/0533 600/301 |
| 2008/0221399 A1 | 9/2008 | Zhou et al. | |
| 2008/0221404 A1 | 9/2008 | Tso | |
| 2008/0275319 A1 | 11/2008 | Van Gogh et al. | |
| 2009/0067690 A1* | 3/2009 | Mainguet | G06K 9/00053 382/124 |
| 2009/0076343 A1 | 3/2009 | James et al. | |
| 2009/0105558 A1 | 4/2009 | Riley-Doucet et al. | |
| 2009/0264713 A1 | 10/2009 | Van Loener et al. | |
| 2010/0036210 A1 | 2/2010 | Chen | |
| 2010/0041965 A1 | 2/2010 | Kang et al. | |
| 2010/0113952 A1 | 5/2010 | Raguin et al. | |
| 2010/0125185 A1 | 5/2010 | Kuo et al. | |
| 2010/0160796 A1 | 6/2010 | Banet et al. | |
| 2010/0168531 A1 | 7/2010 | Shaltis et al. | |
| 2010/0210924 A1* | 8/2010 | Parthasarathy | A61B 5/0002 600/301 |
| 2010/0234701 A1 | 9/2010 | Cho et al. | |
| 2010/0324388 A1 | 12/2010 | Moon et al. | |
| 2011/0066009 A1 | 3/2011 | Moon et al. | |
| 2011/0087080 A1 | 4/2011 | Schroter | |
| 2013/0183646 A1* | 7/2013 | Lusted | G09B 19/00 434/236 |
| 2014/0214115 A1* | 7/2014 | Greiner | A61H 39/002 607/44 |

* cited by examiner

FINGER MOUNTED PHYSIOLOGY SENSOR

CROSS-REFERENCE TO RELATED APPLICATIONS

This application claims priority from U.S. provisional patent application No. 61/792,326 filed Mar. 15, 2013 and entitled "Compact sensor device to acquire multiple physiological signals from the finger", the entire contents of which are incorporated by reference herein.

TECHNICAL FIELD

The application relates generally to biofeedback sensors and, more particularly, to a sensor and a method for capturing different physiological signals from a single finger.

BACKGROUND OF THE ART

The palmar surfaces of fingers and hands are optimal for detecting relevant skin conductance feedback. Fingers are also ideal for sensing other relevant psychophysiological signal types like skin temperature and blood volume pulse (BVP).

In typical biofeedback practice, sensors are usually separately attached to the fingers to detect these types of signal. For example, two sensors are mounted to two different fingers and used to detect or measure skin conductance, a third sensor might be mounted to a third finger and used to measure the temperature of the skin, while a fourth sensor might be mounted to a fourth finger and used to measure BVP.

The use of separate sensors to detect these signals presents certain disadvantages. Firstly, attaching and removing the sensors can require a significant amount of time, and be cumbersome. Secondly, occupying so many fingers of the hand with sensors reduces comfort for the user, and reduces her/his ability to manipulate objects with the occupied hand. Thirdly, using so many sensors can be relatively expensive.

SUMMARY OF THE INVENTION

In one aspect, there is provided a physiology sensor adapted to be worn on a single finger of a wearer, the sensor comprising: a one-finger sensor body having a finger-facing surface and defining a longitudinal axis, the sensor body including first and second raised mounds protruding from the finger-facing surface and being longitudinally spaced-apart such as to define a transverse air gap therebetween, the first and second raised mounds respectively retaining first and second electrodes each defining a skin-abutting electrode surface being raised relative to the finger-facing surface and adapted to abut longitudinally spaced-apart palmar surfaces of the single finger; one or more physiological sensing devices housed within the body, the physiological sensing devices including a skin conductance sensing device operable to measure skin conductance using the first and second electrodes when abutted against the palmar surfaces of the single finger; and a processor housed within the body and in communication with the electrodes and the physiological sensing devices, the processor modulating application of an electrical excitation to the skin conductance sensing device and processing physiological signals captured by the at least one physiological sensing device.

In another aspect, there is provided a physiology sensor adapted to be worn on a single finger of a wearer to capture a number of different physiological signals, the physiology sensor comprising: a one-finger sensor body having a finger-facing surface and defining a longitudinal axis, the sensor body including first and second raised mounds protruding from the finger-facing surface and being longitudinally spaced-apart such as to define a transverse air gap therebetween, the first and second raised mounds respectively retaining first and second electrodes each defining a skin-abutting electrode surface being raised relative to the finger-facing surface and adapted to abut longitudinally spaced-apart palmar surfaces of the single finger; two or more physiological sensing devices housed within the sensor body, the physiological sensing devices comprising: a skin conductance sensing device; and at least one of a temperature sensing device and a photoplethysmography sensing device; the skin conductance sensing device being operable to measure skin conductance using the first and second electrodes, the temperature sensing device being disposed beneath the second electrode and thermally coupled therewith for sensing temperature of the skin abutted against the skin-abutting electrode surface of the second electrode, and the photoplethysmography sensing device including at least one optical sensor disposed beneath the first electrode and optically communicating with the skin abutting against the electrode surface thereof, the electrode surface of the first electrode being adapted to transmit light therethrough; and a processor housed within the body and in communication with the electrodes and the at least two physiological sensing devices, the processor modulating application of an electrical excitation to the skin conductance sensing device and processing physiological signals captured by the at least two physiological sensing devices.

In yet another aspect, there is provided a method for capturing a plurality of different physiological signals from palmar surfaces of a single finger with a physiology sensor, the method comprising: providing the physiology sensor with first and second electrodes mounted to a sensor body, the first and second electrodes having skin-abutting electrode surfaces which are elevated relative to a surface of the body; contacting spaced-apart palmar surfaces of the single finger with the skin-abutting electrode surfaces of the respective first and second electrodes of the sensor; and using the sensor to capture skin conductance and at least one of temperature and blood volume pulse, the step of capturing skin conductance of the skin of the palmar surfaces of the single finger including applying an electrical excitation to the electrodes.

The method described above may further include, in certain embodiments, the following additional features.

Contacting the spaced-apart palmar surfaces may include contacting the palmar surfaces of a distal segment and an adjacent intermediate segment of the single finger with separate electrodes.

Capturing at least temperature of the skin may include thermally coupling a temperature sensing device to the second electrode to measure temperature of the skin abutted thereagainst.

Capturing at least blood volume pulse may include projecting a light beam through one or more openings in the first electrode against the skin of a palmar surface abutted thereagainst, and receiving the light beam returned by the skin of the palmar surface through the same or another opening in the first electrode.

Capturing skin conductance may include applying AC square wave pulses to the electrodes and sampling the electrical excitation at the end of each AC square wave pulse.

Capturing skin conductance may also include wirelessly transmitting captured data on skin conductance, and at least one of temperature of the skin and blood volume pulse.

BRIEF DESCRIPTION OF THE DRAWINGS

Reference is now made to the accompanying figures in which.

DETAILED DESCRIPTION

Figure 1:
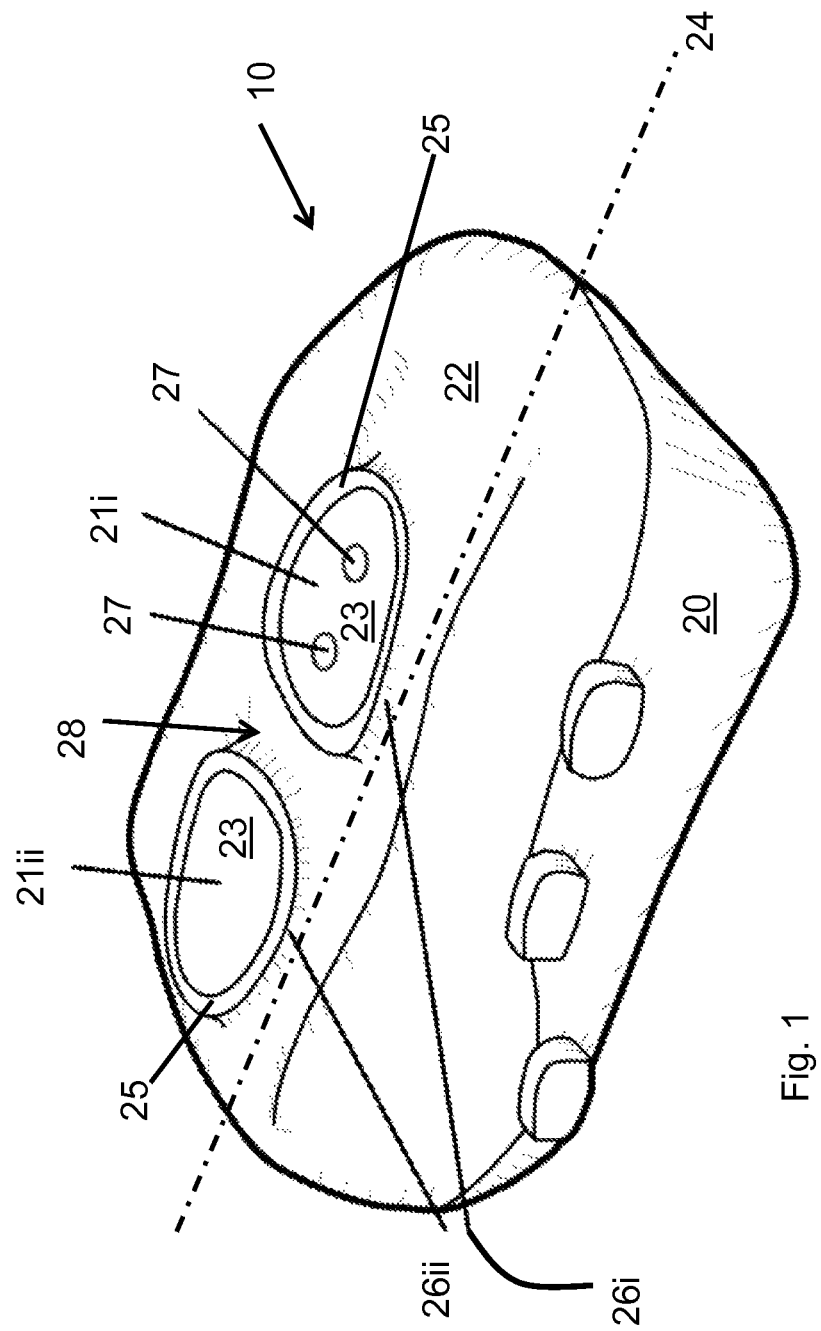
FIG. 1 is a perspective view of a physiology sensor, according to an embodiment.

FIGS. 1 to 4 illustrate generally a sensor 10 which can be mounted to, and removed from, a single finger 60. The sensor 10 is used to detect and capture one or more physiological signals for the general but not exclusive purpose of biofeedback. These physiological signals can be detected and measured with a single sensor 10 mounted to a single finger 60 of a wearer's hand, in contrast to some conventional sensors which require that sensors be mounted to multiple fingers in order to detect or measure the signals in question. The sensor 10 has a sensor body 20 which can be mounted to the finger 60, one or more physiological sensing devices, each of which is operable to sense and/or measure a physiological property, and a processor 50 which controls the application of an electrical excitation and the processing of the data captured by the sensing devices.

The sensor body 20 (or simply "body 20") provides the corpus to the sensor 10, and houses many or all of the components described herein. It can be mounted to, and removed from, the single finger 60 of the wearer. Such mounting can involve the body 20 being attached to the single finger 60, or the single finger 60 being placed on the body 20. This mounting can be facilitated or accomplished with a strap 12 having opposed ends which can be mounted to the body 20 so as to secure it to the single finger 60. The strap 12 can have multiple apertures 11 or holes along its length which facilitate the circulation of air between the single finger 60 and the strap 12 so as to reduce or prevent sweat from accumulating on the skin surface of the single finger 60, which is further discussed below. The body 20 can have one or more attachment members 14 spaced apart on the body 20 so that the strap 12 can attach to the body 20 using different holes along its length, thereby allowing the wearer to vary the tension applied by the strap 12. Such a strap 12 advantageously allows for different single fingers 60 and differently-sized single fingers 60 to be accommodated on the same body 20. It can thus be appreciated that the body 20 is a "one-finger" body 20 because it can be used with only one finger 60 in order to capture or measure one or more physiological signals.

The body 20 can therefore assume the appropriate configuration needed to achieve such functionality, and can be made from any suitable material for this purpose. The body 20 has a finger-facing surface 22 extending along the surface of the body 20 which will face the single finger 60 when the sensor 10 is in use. Since the single finger 60 is elongated along its length, the body 20 is also elongated and defines a longitudinal axis 24, which is not limited to extending along a middle or central portion of the body 20.

The body 20 also includes a first raised mound 26$i$ and a second raised mound 26$ii$ which provide the structure against which the single finger 60 is applied, as further explained below. The term "raised" refers to the protrusion or distancing of the mounds 26$i$,26$ii$ from the finger-facing surface 22 of the body 20, in that the mounds 26$i$,26$ii$ are both elevated with respect to the finger-facing surface 22. The distance at which the mounds 26$i$,26$ii$ protrude from the finger-facing surface 22 is relatively small, for example preferably between about 0.5 mm and about 2.5 mm. Mounds 26$i$,26$ii$ protruding by as much as about 4 mm to about 5 mm are also possible, and the distance can be selected as a function of the aesthetic and ergonomic requirements of the body 20, among other possible factors. The mounds 26$i$,26$ii$ are longitudinally spaced-apart, meaning that they are separated by a distance along the longitudinal axis 24. This separation of the mounds 26$i$,26$ii$ defines an air gap 28 between them, which facilitates the circulation of air between the mounds 26$i$,26$ii$. The air gap 28 also serves to isolate each of the mounds 26$i$,26$ii$, and the electrodes disposed thereon, from one another. As further explained below, this isolation helps to reduce or prevent the growth of the effective electrode surface area, which can otherwise result from the build-up of perspiration on the palmar surfaces.

The first mound 26$i$ and the second mound 26$ii$ retain a first electrode 21$i$ and a longitudinally spaced-apart second electrode 21$ii$, respectively. Each of the electrodes 21$i$,21$ii$ has a skin-abutting electrode surface 23, which is also raised with respect to the finger-facing surface 22, and which enters into contact with the skin of the single finger 60 when mounted to the body 20. The electrode surface 23 of each electrode 21$i$,21$ii$ abuts against the longitudinally spaced-apart palmar surfaces of the single finger 60. The area of the electrode surface 23 can be sufficiently large to enable adequate contact between the palmar surface of the single finger 60 and the electrode surface 23, to enable capture of a psychophysiologically relevant and useful skin conductance signal. The area of the electrode surface 23 can be chosen so that it is small enough to be no larger than the available surface area on the palmar surfaces of the smallest fingers 60 under consideration. Such a criterion helps to ensure that the entire electrode surface 23 would be in contact with the palmar surfaces of the vast majority of fingers 60, which can help to provide a more stable skin conductance reading. In one embodiment, the electrodes 21$i$,21$ii$ are coplanar with each other, at an elevation that is above the finger-facing surface 22. In an alternative embodiment, the first and second electrodes 21$i$,21$ii$ may be disposed at different angular positions relative to each other and/or relative to the finger-facing surface 22. In yet another alternate embodiment, the electrodes 21$i$,21$ii$ are pivotally mounted to their respective mounds 26$i$,26$ii$, such that the electrodes 21$i$,21$ii$ appear to float above the finger-facing surface 22, and can be selectively angled with respect thereto in order to better conform to the surfaces of each of the abutted palmar surfaces of the finger. As such, the electrodes 21$i$,21$ii$ may not necessarily be coplanar, especially when pivoted to form different angles with the finger-facing surface 22.

It can therefore be appreciated that since the electrodes 21$i$,21$ii$ are themselves spaced apart on their respective mounds 26*i*,26*ii* along the length of the body 20, they will therefore abut against the palmar surfaces of the single finger 60 at similarly spaced-apart positions. The spaced-apart positions of the palmar surface can be defined on a same finger segment or phalange of the single finger 60, or generally more often, on separate finger segments of the single finger 60. For example, and in reference to FIG. 4, the electrode surfaces 23 of each electrode 21*i*,21*ii* can abut against the palmar surface of adjacent finger segments, such as the palmar surface of the distal finger segment 16 and the palmar surface of the intermediate finger segment 18. In such a configuration, the air gap 28 is aligned with the joint connecting the distal and intermediate finger segments 16,18. Alternatively, the electrode surfaces 23 of each electrode 21*i*,21*ii* can abut against the palmar surface of the distal finger segment 16 and the palmar surface of the proximal finger segment 17.

Figure 3:
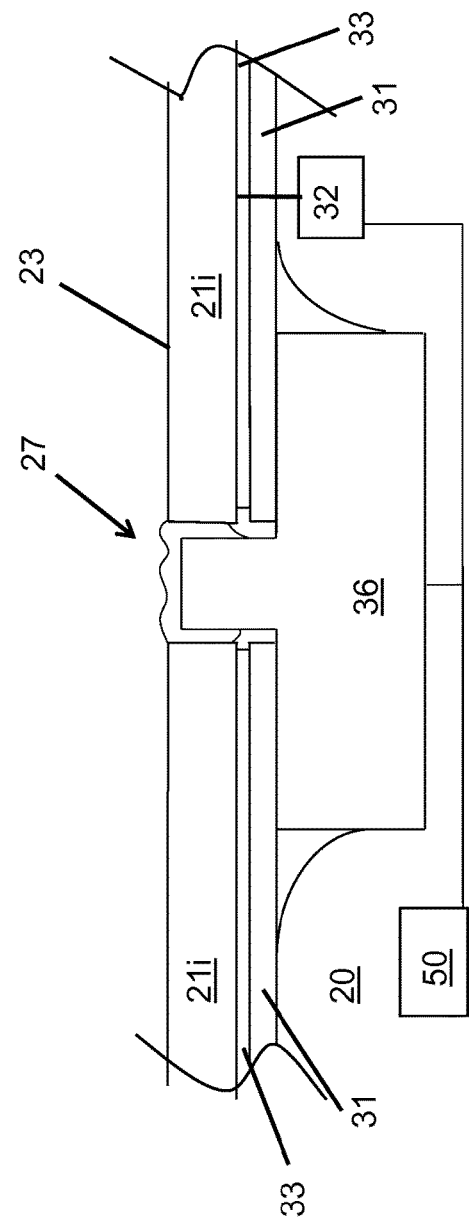
FIG. 3 is a cross-sectional view of another part of the sensor of FIG. 1.
Figure 4:
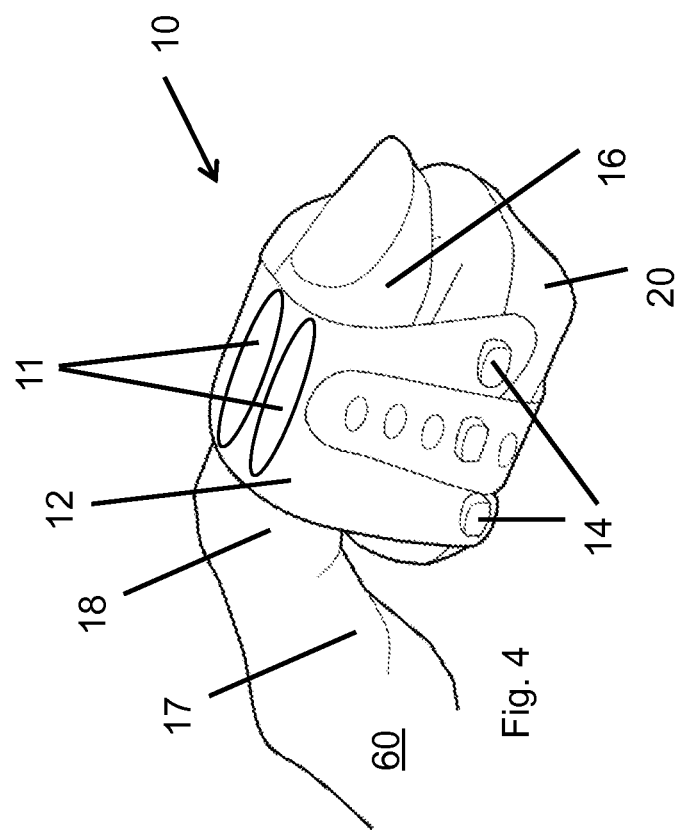
FIG. 4 is a perspective view of the sensor of FIG. 1 having a strap and being shown mounted to a finger.

Referring to FIG. 3, one of the electrodes 21*i*,21*ii*, typically the first electrode 21*i*, may have one or more openings 27 extending through the electrode surface 23. The openings 27 allow for the transmission and receipt of light therethrough, as will be further described below. One or more of the openings 27 can be sealed so as to prevent the ingress of debris or fluids, while still allowing for the light to be transmitted therethrough. Such sealing can be achieved with a glass or plastic lens, or with a suitable epoxy as shown in FIG. 3, among other possibilities.

Each electrode 21*i*,21*ii* serves as a platform which facilitates the measurement of the one or more different physiological signals. The electrodes 21*i*,21*ii* can be any surface which act as an electrical conductor so as to permit a flow of electric current to and from the skin of the single finger 60. As such, at least the electrode surfaces 23 can be made of any suitable conductive and biocompatible material, such as stainless steel or gold. The electrodes 21*i*,21*ii* can also be made of a plated or metal alloy, such as gold-plated copper. Similarly, the electrodes 21*i*,21*ii* can take any suitable configuration to achieve such functionality. For example, the electrodes 21*i*,21*ii* shown in the embodiment of FIG. 1 are substantially "egg-shaped", where the wider portions of the electrodes 21*i*,21*ii* are disposed relatively close to one another across the air gap 28, and where the thinner portions are disposed further away from one another. Such a shape of the electrodes 21*i*,21*ii* can be ergonomically suitable for differently-sized single fingers 60. The size of the electrodes 21*i*,21*ii* can also vary. In one possible embodiment, each electrode 21*i*,21*ii* can have approximate dimensions of about 10 mm×12 mm, and they can be longitudinally spaced-apart, center to center, by about 18 mm. The distance between the closest points of the two electrodes 21*i*,21*ii* can be approximately 6 mm.

The electrode surfaces 23 of each of the electrodes 21*i*,21*ii* can be circumscribed by correspondingly shaped and relatively thin non-conductive peripheral rims 25, which surround the raised electrodes surfaces 23. While the electrodes may be mounted to the raised mounds of the sensor body such that no such rims are present, the thinness of the non-conductive region or the rim 25, when present, can help to control the quantity of conductive electrode surface 23 area in contact with the skin, and can help to limit the potential growth in effective skin area through sweat accumulation on non-conductive surfaces adjacent to the electrodes 21*i*,21*ii*. The expression "non-conductive" refers to the ability of the peripheral rims 25 to prevent or significantly reduce the conductance of electric current therethrough. In most instances, such non-conductivity is derived from the material composition of the peripheral rims 25, which can be the same as that of the body 20. The peripheral rims 25 can be coplanar with the electrode surfaces 23, slightly elevated with respect to the electrode surfaces 23, or lower than the electrode surfaces 23, as required.

At least the spacing of the electrodes 21*i*,21*ii* and their elevation with respect to the finger-facing surface 22 can help to prevent the onset or accumulation of perspiration on the surface of the skin of the single finger 60. The apertures in the strap 12, as well as the relative thinness of the non-conductive peripheral rims 25 which surround their electrode surfaces 23, can also contribute. The prevention or reduction of perspiration on the skin of the single finger 60 helps to improve or maintain the psychophysiological relevance of the skin conductance readings, which is one of the different physiological signals which the sensor 10 can capture.

Skin conductance is typically measured by passing a current through the skin. In most conventional sensors, electrodes are placed on separate fingers, and the current is passed through the hand between these fingers. However, where the electrodes are mountable to the same finger and in proximity to one another, there is a risk of skin conductance "sweat bridging". Sweat bridging occurs when sweat builds up on the surface of the skin between adjacent electrodes such that the current used to excite the electrodes is able to travel directly between the electrodes along the moisture path created by the sweat, and thus not through the skin. Sweat bridging therefore reduces the psychophysiological relevance of the skin conductance readings, and can lead to inaccurate measurements. Similarly, when electrodes are adjacent to, and approximately co-planar with, a larger non-conductive surface, sweat can accumulate on the skin surface in contact with this adjacent non-conductive surface because this skin surface lacks air circulation. Furthermore, if sweat is allowed to accumulate over the area of skin surrounding one or the other electrode (even if not directly between the two electrodes), current can flow out from the periphery of the electrodes into the moist area surrounding the pads, then into the skin in contact with this surrounding area. This phenomenon can effectively increase the surface area of the skin conducting the excitation current, and affect the psychophysiological relevance of the conductance reading.

The sensor 10 disclosed herein is able to palliate or overcome these phenomena because the electrodes 21*i*,21*ii* are spaced apart and raised across the air gap 28, which isolates the electrodes 21*i*,21*ii* from one another, and encourages or allows the circulation of air between the electrodes 21*i*,21*ii*, thus allowing for evaporative drying to occur on the surface of the skin of the single finger 60. Furthermore, if present, the thinness or minimal dimensions of the non-conductive peripheral rims 25 surrounding of the electrode surfaces 23 minimises the skin's contact with non-electrode surfaces when compared to thicker peripheral boundaries. In so doing, the peripheral rims 25 help to ensure that the only significant contact the skin of the single finger 60 makes with the body 20 is against the electrode surfaces 23. It can therefore be appreciated that in minimising or eliminating these phenomena, the sensor 10 can help to achieve more psychophysiological relevant measurements of the conductance of the skin of the single finger 60.

The sensor 10 has one or more physiological sensing devices. While the sensing devices may share components in the signal chain, each of the sensing devices can be selectively operated independently of the others in order to measure the desired physiological property. All of the sensing devices are housed within the body 20 and thus do not enter into direct contact with the palmar surfaces of the single finger 60. This positioning of the sensing devices within the body 20 prevents them from interfering with the electrodes 21i,21ii, thus allowing the electrodes 21i,21ii to measure the skin conductance of the single finger 60 unimpeded. Furthermore, the sheltering of the sensing devices within the body 20 protects them from abrasion and corrosion.

Figure 2:
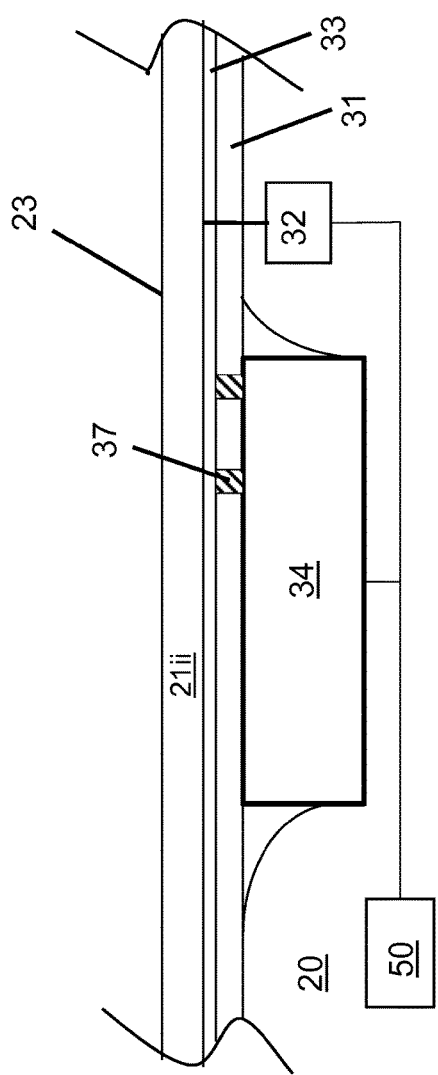
FIG. 2 is a cross-sectional view of a part of the sensor of FIG. 1.

It will be appreciated that up to three sensing devices are disclosed herein, but the sensor 10 can have as few as one sensing device or more than three sensing devices as may be required for sensing physiological properties which are the same or different than the ones disclosed. The term "sensing" refers to the ability of the sensing devices to perform any one or a combination of, detecting, capturing, or measuring the physiological signals, as required. Referring to FIGS. 2 and 3, the sensing devices of the sensor 10 include at least a skin conductance sensing device 32 as well as, one or both of a temperature sensing device 34 and a photoplethysmography (or PPG) sensing device 36. Accordingly, in one embodiment the sensor 10 may include only a skin conductance sensing device 32. In another embodiment, the sensor 10 may include a skin conductance sensing device 32, in addition to a temperature sensing device 34. In yet another embodiment, the sensor may include skin conductance sensing device 32, in addition to a PPG sensing device 36. In yet a further embodiment, and as depicted in FIGS. 1-4, the sensor 10 includes all three sensing devices, namely a skin conductance sensing device 32, a temperature sensing device 34 and a photoplethysmography (PPG) sensing device 36.

The skin conductance sensing device 32 is housed within the body 20, and cooperates with, and may be integral to, both of the first and second electrodes 21i,21ii. It uses the electrodes 21i,21ii to measure the conductance of the skin of the single finger 60 when the electrode surfaces 23 are in contact with the palmar surfaces of the single finger 60. The measured skin conductance can be used for detecting stress responses, among other possibilities. In a typical operation, skin conductance is measured by passing an electric current through the electrode surface 23 of either one of the first or second electrode 21i,21ii, then through the skin contacting this electrode surface 23. The current then goes through this skin, into a relatively low resistance area inside the single finger 60, and exits the inside of the single finger 60 via the skin in contact with the other electrode surface 23 of the other electrode 21i,21ii, and through a reference resistor to an equipotential point. The skin conductance can then be determined from the ratio between the total applied voltage and the voltage appearing across the reference resistor or that appearing across the electrodes 21i,21ii.

The temperature sensing device 34 is also housed within the body 20, and is disposed beneath one of the electrodes 21i,21ii, typically the second electrode 21ii. The temperature sensing device 34, which can be a thermistor, is thermally coupled to the second electrode 21ii and is used to measure the temperature of the skin which abuts against the electrode surface 23 of the second electrode 21ii. Since the electrode surface 23 of the second electrode 21ii is in good thermal and electrical contact with the palmar surface of the single finger 60 when abutted against it, it is advantageous to use the second electrode 21ii to capture skin temperature. In this regard, the thickness of the second electrode 21ii can be thinner than that of the first electrode 21i in order to facilitate heat transfer from the palmar surface to the temperature sensing device 34. However, it is not optimal to place the temperature sensing device 34 directly on this electrode surface 23 because it will occupy an important area of the electrode surface 23 and prevent it from properly measuring skin conductance. Therefore, the temperature sensing device 34 is placed away from the second electrode 21ii inside the body 20, and thermally coupled to the second electrode 21ii. The expression "thermally coupled" refers to the conductive heat transfer link formed between the palmar surface of the finger 60 and the temperature sensing device 34. This link helps to capture the heat transferred by the palmar surface of the single finger 60. This link or connection can take many forms. For example, multiple circuit board vias 37 can be used to thermally link the temperature sensing device 34 to the second electrode 21ii. In another possible configuration, a circuit board 31 or flexible board can also be housed within the body 20 and placed between the sensing devices and the electrodes 21i,21ii. The temperature sensing device 34 can be soldered to the circuit board 31, and the circuit board 31 can be attached to the underside or sensor body-facing surface of the electrodes 21i,21ii with a thermally and electrically conductive adhesive layer 33. This indirect contact between the temperature sensing device 34 and the second electrode 21ii thus allows for stable and consistent measurements of the temperature of the skin on the palmar surface in contact with the second electrode 21ii, while minimising or preventing interference with the ability of the second electrode 21ii to measure skin conductance. In so doing, the temperature sensing device 34 is able to provide the second electrode 21ii with at least a dual functionality.

The PPG sensing device 36 is also housed within the body 20. The PPG sensing device 36 is operable to optically detect a change in blood volume, and in particular, may be used to detect the blood volume pulse (BVP) from a palmar surface of the single finger 60. In so doing, the PPG sensing device 36 can be used to detect heartbeats, and thus, measure the wearer's heart rate. The PPG sensing device 36 can have one or more optical sensors disposed beneath the first electrode 21i, which has one or more openings 27 extending through its electrode surface 23. The PPG sensing device 36 is able to optically communicate with the palmar surface of the single finger 60 via these one or more openings 27 by sending light to impact the palmar surface through the one or more openings 27, and by receiving returned light therefrom. Each of the optical sensors or optodes therefore can generate or receive a light beam. Optionally, and referring to FIG. 5, the PPG sensing device 36 can be a pairing of an optical emitter 35 and an optical receiver 39. The optical emitter 35 or LED, which emits a visible or infrared light through one or more of the openings 27, and an optical receiver 39, which receives the same light through the same or another one of the openings 27 as reflected by the skin of the palmar surface of the single finger 60.

The positioning of the temperature sensing device 34 within the body 20 beneath the second electrode 21 ii and the position of the PPG sensing device 36 within the body 20 beneath the first electrode 21i can provide several advantages, particularly when the first electrode 21i and the second electrode 21ii are adapted to abut against the distal finger segment 16 and the intermediate finger segment 18 of the single finger 60, respectively. Firstly, positioning the PPG sensing device 36 to optically communicate with the palmar surface of the distal finger segment 16 appears to provide more stable and consistent BVP readings. Secondly, the positioning of the temperature sensing device 34 and the PPG sensing device 36 to communicate with the intermediate and distal finger segments 18,16, respectively, allows for the body 20 of the sensor 10 to be moved away from the junction of the single finger 60 to its hand, thereby allowing for increased mobility and utility of this single finger 60 about its junction with the hand or improved comfort of the wearer. Thirdly, the positioning of the temperature sensing device 34 and the PPG sensing device 36 to communicate with adjacent finger segments positions the electrodes 21i, 21ii and the air gap 28 across a finger joint connecting these two finger segments, which can further facilitate the evaporative drying discussed above.

Figure 5:
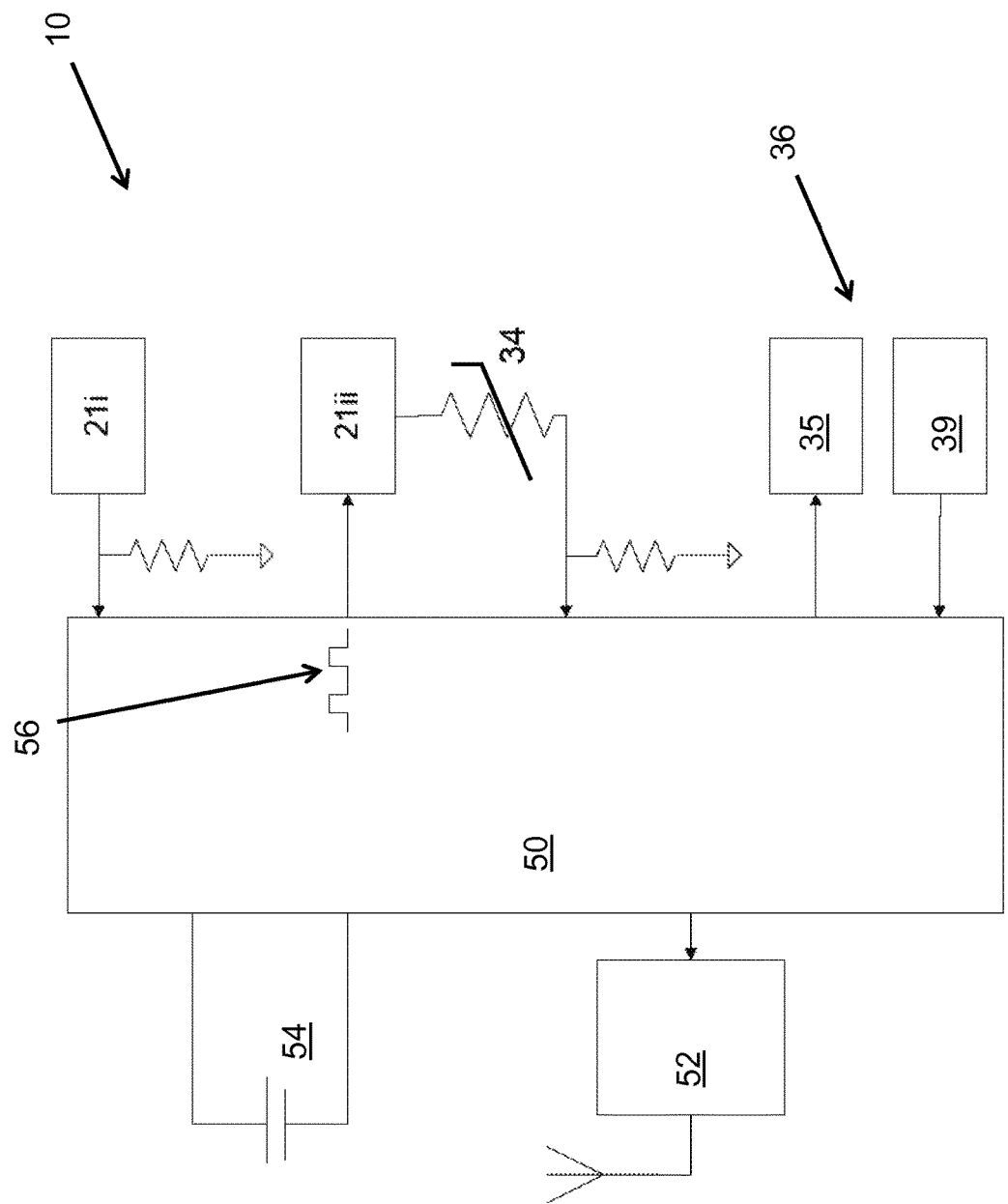
FIG. 5 is a block diagram showing components of the physiology sensor of FIG. 1.

Referring to FIG. 5, the sensor 10 also has a processor 50 housed within the body 20, or mounted thereto. The processor 50 can be a microcontroller or other electronic circuit which applies an electrical excitation to the one or more sensing devices, and communicates with the electrodes 21i,21ii and sensing devices to process the physiological signals they capture. The processor 50 is programmed to control the supply of the electrical excitation. Similarly, the term "process" refers to the ability of the processor 50 to receive the raw data captured by the sensing devices, temporarily store this data in a suitable computable data storage, and transmit the data wirelessly or otherwise to a remote processing unit for manipulation or display. The wireless transmission of raw data can be accomplished using a wireless communication module 52 integrated with the processor 50 or separate therefrom, such as a Bluetooth® module, or by using WiFi®. The processor 50 has a power source 54, which can be a battery or a lithium cell, housed within the body 20 which powers the sensor 10, thus allowing it to operate. In most embodiments, the processor 50 supplies the electrical excitation directly to the sensing devices. The electrical excitation applied can be steady-state DC or AC current. When measuring skin conductance with the skin conductance sensing device 32 and the electrodes 21i,21ii, the long term application of DC excitation can lead to electrode polarization, where the electrodes charge up like a battery and oppose the flow of current, thus reducing the apparent skin conductance and skewing skin conductance readings.

When necessary to overcome or palliate this effect, the processor 50 can apply a relatively low-frequency excitation using an AC square wave generator 56, which can apply an AC square wave pulse to the electrodes 21i,21ii and the sensing devices. The resultant skin conductance measurement can be determined from measuring or sampling the difference between the voltage at the ends of alternating AC square wave pulses. It is known that skin has a significant capacitive component, meaning that after a step in the applied voltage, steady state DC current is not established right away and instead drops off from an initial higher level as the skin capacitance changes. Since conventional measurement techniques use DC current, the sensor 10 disclosed herein can sample the resultant AC excitation after the maximum amount of settling time has elapsed, such as just before the next voltage reversal. The use of AC electrical excitation furthermore facilitates the nulling of amplifier offset in the sensing circuit, and also advantageously allows for a higher level excitation to be used because the applicable medical standards allow higher limits for AC excitation compared to DC excitation. The use of this higher level AC excitation can provide lower noise skin conductance readings.

A typical skin conductance measurement operation using AC excitation can be as follows. A low frequency AC square wave excitation is applied to the electrodes 21i,21ii in series with a resistor, thereby forming a voltage divider. The resultant voltage between the electrodes 21i,21ii is measured at the end of each half cycle, and the difference is taken as a peak to peak voltage. Skin conductance can be determined from the ratio between the voltage applied to the entire voltage divider and the voltage appearing across the electrodes 21i,21ii, by computation either by the processor 50 or in an associated application program.

Having described at least some of the features of the sensor 10, a method 100 for capturing a plurality of different physiological signals with a physiology sensor will now be described in reference to FIG. 6.

Figure 6:
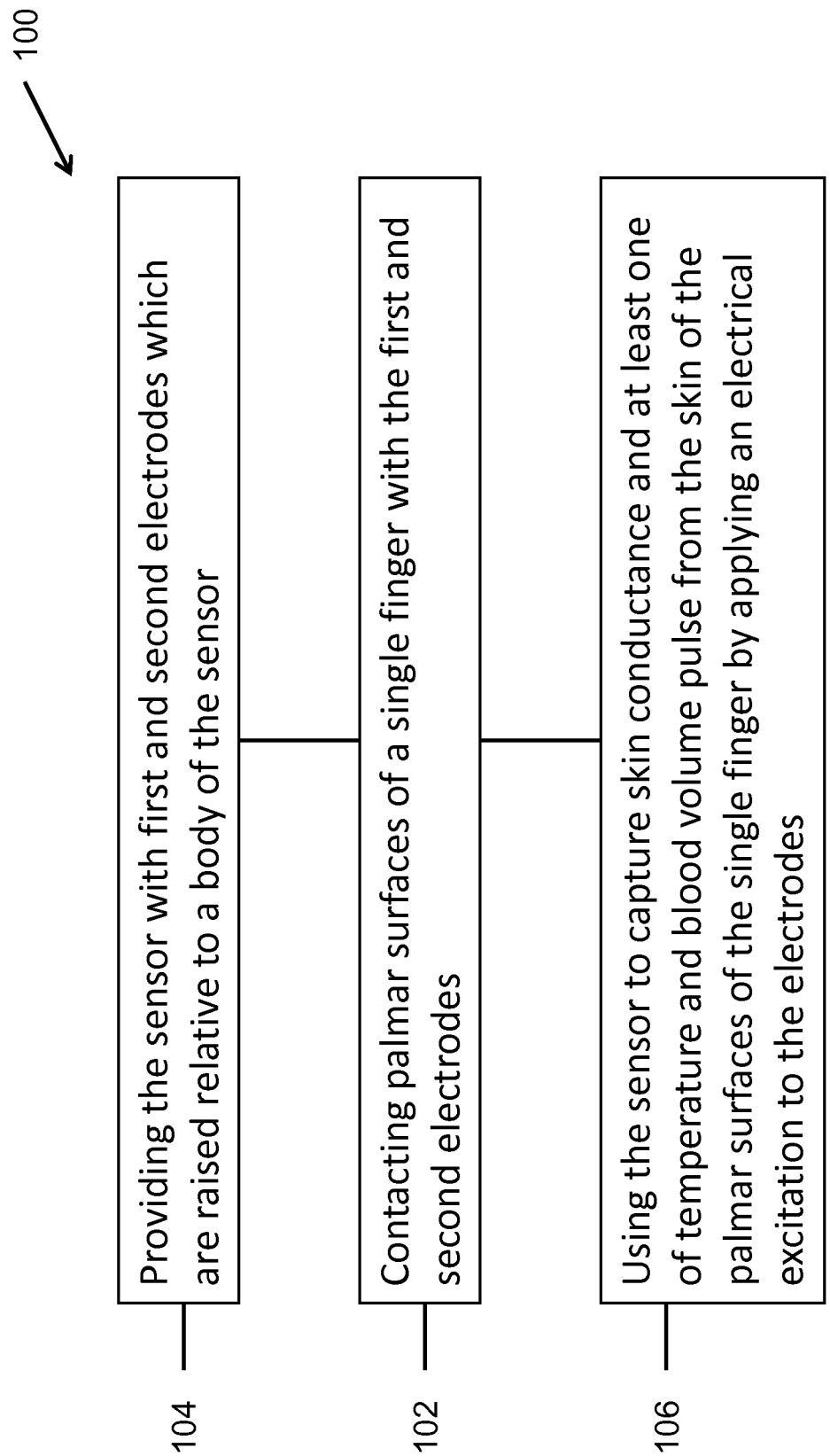
FIG. 6 is a flow diagram of a method for capturing a plurality of different physiological signals from spaced-apart palmar surfaces of a single finger with a sensor.

The method 100 includes contacting spaced-apart palmar surfaces of the single finger with respective first and second raised electrodes of the sensor, shown as 102 in FIG. 6. Such contact with the thermally and electrically conductive electrodes allows for the one or more different physiological signals to be captured. This contacting can include securing the palmar surfaces to the body of the sensor with a strap, and can also include contacting the palmar surface of a distal segment and an adjacent intermediate segment of the single finger with separate electrodes.

The method 100 also includes distancing the contacted spaced-apart palmar surfaces of the single finger from a body of the sensor, shown as 104 in FIG. 6. This distancing is generally achieved with the structure of the body of the sensor itself.

The method 100 also includes capturing skin conductance of the skin of the palmar surfaces of the single finger by applying an electrical excitation to the electrodes, and capturing at least one of temperature of the skin and blood volume pulse, shown as 106 in FIG. 6. This can include applying an electrical excitation to allow the sensing devices to capture their respective physiological signals. The application of the electrical excitation can include applying AC square wave pulses to the electrodes, or to the sensing devices, such as via a resistor. The application of the electrical excitation can further include sampling the electrical excitation at the end of each AC square wave pulse in order to determine the skin conductance of the palmar surface of the single finger.

The method 100 can also include measuring conductance of the skin with the first and second electrodes, thermally coupling a temperature sensing device to the second electrode to measure temperature of the skin abutted thereagainst, and generating a light beam with a PPG sensing device which projects through an opening of the first electrode. Diffused light is received back through the same or another opening, from the skin of the palmar surface, to be captured by an optical receiver, in order to detect the BVP. The capturing in 106 therefore allows for the capturing of the skin conductance of the palmar surface of the skin, and at least one other physiological signals (i.e. skin temperature, and BVP) with independent sensing devices.

The capturing of 106 can include thermally coupling the temperature sensing device to the second electrode when it is in contact with the palmar surface of the intermediate segment of the single finger. Similarly, generating the light beam can include directing the light beam against the palmar surface of the distal segment of the single finger and receiving a reflected light beam from this palmar surface. In addition, measuring the conductance of the skin can include measuring the difference in voltage at the end of alternating AC square wave pulses, such as those applied by an AC square wave generator.

Further optionally, capturing the conductance of the skin can include marking or detecting a reduction in contact between one or more of the palmar surfaces and the corresponding electrode against which it is abutted. It is known that in conditions of relatively extreme motion of the single finger and the affixed sensor, the skin of the palmar surfaces may momentarily separate from the electrodes, thereby reducing the surface area of the skin in contact with the electrodes and resulting in a momentary decrease in measured skin conductance. When this momentary decrease in skin conductance occurs, it is typically also accompanied by a deviation in the BVP signal, such as a spike or a significant decrease. This can be misleading because the deviation in the BVP signal is not necessarily indicative of any physiological event occurring in the wearer, and can thus lead to inaccurate or missing heart rate readings. It is therefore desirable to mark or detect these misleading BVP readings so that they can be identified and disregarded when the raw data of the physiological signal measurements is analysed. One possible technique for detecting these misleading BVP readings is to identify the skin conductance measurements which are suggestive of a reduced skin contact with the electrodes. These identified skin conductance measurements can be algorithmically combined with the misleading BVP readings so that the misleading BVP readings can be excluded, or marked as suspect.

The above description is meant to be exemplary only, and one skilled in the art will recognize that changes may be made to the embodiments described without departing from the scope of the invention disclosed. For example, although the sensor 10 disclosed herein is shown mounted to the index finger, it can be appreciated that it can be mounted to any other single finger 60 or the thumb. Still other modifications which fall within the scope of the present invention will be apparent to those skilled in the art, in light of a review of this disclosure, and such modifications are intended to fall within the appended claims.

The invention claimed is:

1. A physiology sensor adapted to be worn on a single finger of a wearer, the sensor comprising:
    a one-finger sensor body having a finger-facing surface and defining a longitudinal axis, the sensor body including first and second raised mounds protruding from the finger-facing surface and being longitudinally spaced-apart such as to define a transverse air gap therebetween, the first and second raised mounds respectively retaining first and second electrodes each defining a skin-abutting electrode surface being raised relative to the finger-facing surface and adapted to abut longitudinally spaced-apart palmar surfaces of the single finger, one of the first and second electrodes having one or more openings in the skin-abutting electrode surface thereof, the skin-abutting electrode surfaces being at an elevation greater than an elevation of a remainder of the sensor body to position the spaced-apart palmar surfaces of the single finger above the sensor body;
    one or more physiological sensing devices housed within the body, the physiological sensing devices including a skin conductance sensing device operable to measure skin conductance using the first and second electrodes when abutted against the palmar surfaces of the single finger, the physiological sensing devices also including a photoplethysmography sensing device having an optical emitter and an optical receiver both disposed beneath said one of the first and second electrodes having the openings in the skin-abutting electrode surface, the optical emitter being operable to generate a light beam to project through at least one of said openings against the skin abutting against the electrode surface thereof, and the optical receiver being operable to receive the light beam returned by the skin through the same or another one of said openings; and
    a processor housed within the body and in communication with the electrodes and the physiological sensing devices, the processor modulating application of an electrical excitation to the skin conductance sensing device and processing physiological signals captured by the physiological sensing devices.

2. The physiology sensor as defined in claim 1, wherein the physiological sensing devices further include a temperature sensing device, the temperature sensing device comprising a thermistor disposed beneath the second electrode and thermally coupled therewith for sensing temperature of the skin abutted against the skin-abutting electrode surface of the second electrode.

3. The physiology sensor as defined in claim 2, wherein the first electrode has the one or more openings in the skin-abutting electrode surface thereof, and the optical emitter and the optical receiver are both disposed beneath the first electrode.

4. The physiology sensor as defined in claim 1, wherein the first electrode has the one or more openings in the skin-abutting electrode surface thereof, and the optical emitter and the optical receiver are both disposed beneath the first electrode.

5. The physiology sensor as defined in claim 1, wherein the mounds each protrude from the finger-facing surface of the body a distance of between 0.5 mm and 2.5 mm.

6. The physiology sensor as defined in claim 1, wherein each of the first and second raised mounds has a non-conductive peripheral rim which circumscribes the electrode surface of each of the first and second electrodes.

7. The physiology sensor as defined in claim 1, wherein the processor includes an AC square wave generator communicating with at least the first and second electrodes to apply AC square wave pulses thereto.

8. The physiology sensor as defined in claim 1, wherein the skin-abutting electrode surface of each of the first and second electrodes is substantially egg-shaped and defines a wide end and a thin end, the wide ends of the skin-abutting electrode surfaces being positioned adjacent one another across the air gap.

9. The physiology sensor as defined in claim 1, wherein the first and second electrodes are longitudinally spaced apart a distance corresponding to a distance between the palmar surfaces of a distal segment and an adjacent intermediate segment of the single finger.

10. The physiology sensor as defined in claim 1, wherein the processor includes a circuit board housed within the body, the circuit board being secured to an inwardly facing surface of at least one of the first and second electrodes with a thermally and electrically conductive adhesive.

11. The physiology sensor as defined in claim 1, wherein the processor includes a wireless communication module operable to wirelessly transmit data captured by the physiological sensing devices.

12. The physiology sensor as defined in claim 1, further comprising an elongated strap having opposed ends fastenable to the body for securing the body to the single finger, the strap having a plurality of air-flow apertures therein spaced apart along at least a portion of a length of the strap.

13. A physiological sensor adapted to be worn on a single finger of a wearer to capture a number of different physiological signals, the physiology sensor comprising:
    a one-finger sensor body having a finger-facing surface and defining a longitudinal axis, the sensor body including first and second raised mounds protruding from the finger-facing surface and being longitudinally spaced-apart such as to define a transverse air gap therebetween, the first and second raised mounds respectively retaining first and second electrodes each defining a skin-abutting electrode surface being raised relative to the finger-facing surface and adapted to abut longitudinally spaced-apart palmar surface of the single finger, one of the first and second electrodes having one or more openings in the skin-abutting electrode surface thereof;

two or more physiological sensing device housed within the sensor body, the physiological sensing device comprising: a skin conductance sensing device; and at least one of a temperature sensing device and a photoplethysmography sensing device; the skin conductance sensing device being operable to measure skin conductance using the first and second electrodes, the temperature sensing device being disposed beneath the second electrode and thermally coupled therewith for sensing temperature of the skin abutted against the skin-abutting electrode surface of the second electrode, and the photoplethysmography sensing device including an optical emitter and an optical receiver both disposed beneath said one of the first and second electrodes having the openings in the skin-abutting electrode surface, the optical emitter being operable to generate a light beam to project through at least one of said openings against the skin abutting against the electrode surface thereof, and the optical receiver being operable to receive the light beam returned by the skin through the same or another one of said openings; and a processor housed within the body and in communication with the electrodes and the at least two physiological sensing devices, the processor modulating application of an electrical excitation to the skin conductance sensing device and processing physiological signals captured by the at least two physiological sensing devices.

14. The physiology sensor as defined in claim 13, wherein the mounds each protrude from the finger-facing surface of the body a distance of between 0.5 mm and 2.5 mm.

15. The physiology sensor as defined in claim 13, wherein each of the first and second raised mounds has a non-conductive peripheral rim which circumscribes the electrode surface of each of the first and second electrodes.

16. The physiology sensor as defined in claim 13, wherein the temperature sensing device is a thermistor in conductive heat transfer communication with the second electrode.

17. The physiology sensor as defined in claim 13, wherein the processor has an AC square wave generator communicating with at least the first and second electrodes to apply AC square wave pulses thereto.

18. The physiology sensor as defined in claim 13, wherein the processor has a wireless communication module operable to wirelessly transmit data captured by the at least one physiological sensing device.

19. The physiology sensor as defined in claim 13, further comprising an elongated strap having opposed ends mountable to the sensor body for securing the body to the single finger, the strap having a plurality of apertures spaced apart along a length of the strap.

20. A method for capturing a plurality of different physiological signal from palmar surfaces of a single finger with physiology sensor, the method comprising:

providing the physiology sensor with first and second electrodes mounted to a sensor body, the first and second electrodes having skin-abutting electrode surfaces which are elevated relative to a surface of the body, the skin-abutting electrode surfaces being at an elevation greater than an elevation of a remainder of the sensor body to position the palmar surfaces of the single finger above the sensor body, one of the first and second electrodes having one or more openings in the skin-abutting electrode surface thereof;

contacting spaced-apart palmar surfaces of the single finger with the skin-abutting electrode surfaces of the respective first and second electrodes of the sensors; and using the sensor to capture skin conductance and using the sensor to capture and at least one of temperature and blood volume pulse with one or more physiological sensing devices housed within the sensor and disposed beneath the skin-abutting electrode surface of at least one of the first and second electrodes, the step of capturing skin conductance of the skin of the palmar surfaces of the single finger including applying an electrical excitation to the electrodes, and the step of capturing blood volume pulse including emitting a light beam through at least one of said openings in the skin-abutting electrode surface and receiving the light beam returned by the skin throught the same or another one of said openings in the skin-abutting electrode surface.

* * * * *